United States Patent [19]

Blytas et al.

[11] 4,356,155
[45] Oct. 26, 1982

[54] SULFUR PROCESS

[75] Inventors: George C. Blytas; Zaida Diaz, both of Houston, Tex.

[73] Assignee: Shell Oil Company, Houston, Tex.

[21] Appl. No.: 267,197

[22] Filed: May 26, 1981

[51] Int. Cl.³ ............................................. B01D 53/34
[52] U.S. Cl. ................................ 423/226; 423/573 R; 423/573 G
[58] Field of Search .............. 423/224, 226, 573, 575, 423/222, 578 R

[56] References Cited

U.S. PATENT DOCUMENTS 3,068,065 12/1972 Hartley et al. .................. 423/228
3,099,536 7/1963 Urban et al. .................... 423/575
3,622,273 11/1971 Roberts et al. .................. 423/573
3,933,993 1/1976 Salemme ......................... 423/226
4,009,251 2/1977 Meuly ............................. 423/573
4,091,073 5/1978 Winkler .......................... 423/226

Primary Examiner—Earl C. Thomas
Attorney, Agent, or Firm—Albert J. Adamcik

[57] ABSTRACT

A cyclic process for the removal of hydrogen sulfide from a variety of gas streams is disclosed. The gas stream containing the sour gases is contacted with a solution of the Fe(III) chelate of nitrilotriacetic acid and a modifier having the formula $C_nH_{2n-1}OH$, wherein n is a whole number from 4 through 22. The hydrogen sulfide is converted to sulfur, and the Fe(III) chelate is converted to the Fe(II) chelate. The process includes sulfur removal and regeneration of the Fe(III) chelate.

14 Claims, No Drawings

SULFUR PROCESS

BACKGROUND OF THE INVENTION

The presence of significant quantities of $H_2S$ and $CO_2$ in various "sour" industrial gaseous streams poses a persistent problem. Although various procedures have been developed to remove and recover these contaminants, most such processes are deficient, for a variety of reasons.

In one cyclic method currently attracting attention, the sour gas is contacted, preferably with a solvent-reactant system which comprises a regenerable reactant, to produce solid free sulfur which is recovered either prior or subsequent to regeneration. Suitable reactant materials include polyvalent metallic ions, such as iron, vanadium, copper, manganese, and nickel, and include polyvalent metal chelates. Preferred reactants are coordination complexes in which the polyvalent metals form chelates with specified organic acids.

In yet another process, e.g., that disclosed in U.S. Pat. No. 4,091,073, issued May 23, 1978, to Winkler, $CO_2$ present in the gaseous stream is also removed by the use of a suitable selective absorbent.

A problem associated with such processes is that the solid sulfur produced is of poor quality, i.e., it is very finely divided and difficult to separate from the aqueous reactant solution. A process which provided for the efficient reaction of $H_2S$ and removal of the sulfur produced could have great economic importance.

SUMMARY OF THE INVENTION

Accordingly, the invention relates to a process for the removal of $H_2S$ from a sour gaseous stream comprising contacting the sour gaseous stream in a contacting zone with an aqueous reactant mixture, at a temperature below the melting point of sulfur, the aqueous reactant mixture comprising an effective amount of the Fe(III) chelate of nitrilotriacetic acid and a modifying amount of a composition selected from compounds having the formula $C_nH_{2n-1}OH$, wherein n is a whole number from 4 through 22, and mixtures thereof. A sweet gas stream is produced, and an aqueous admixture containing crystalline sulfur and a reduced reactant is removed from the contact zone. At least a portion of the sulfur crystals may be removed before regenerating the reactant, or at least a portion of the sulfur crystals may be removed after regeneration. The sulfur crystals obtained, due to the presence of the modifier compound, are of improved quality, i.e., they have increased size, and, thus, improved filterability. The reduced reactant, i.e., the Fe(II) chelate of nitrilotriacetic acid, is regenerated by contacting the mixture in a regeneration zone or zones with oxygen. The term "oxygen", as used herein, includes oxygen-containing gases, such as air or air-enriched with oxygen. The oxygen oxidizes the reduced metal ions of the chelate to the higher valence state, and the regenerated mixture is returned to the contact zone.

In another embodiment of the invention, a sour gaseous stream containing $H_2S$ and $CO_2$ is contacted with a selective absorbent-aqueous reactant mixture at a temperature below the melting point of sulfur, the reactant mixture and procedure being similar to that described, supra. Broadly, this is accomplished by the use of an absorbent mixture containing a selective absorbent for $CO_2$ (and preferably for $H_2S$, as well), an effective amount of the Fe(III) chelate of nitrilotriacetic acid, and a modifying amount of the modifiers described. A purified or "sweet" gaseous stream is produced which meets general industrial and commercial $H_2S$ and $CO_2$ specifications. The $CO_2$ is absorbed and the $H_2S$ is immediately converted to sulfur by the polyvalent metal chelate. In the process, the Fe(III) chelate is reduced, and the sulfur may be treated, as described, supra. As in the previous embodiment, the sulfur crystals may be removed prior or subsequent to a regeneration of the admixture, and the crystals produced are of increased size. Preferably, if the volume of $CO_2$ absorbed is large, the reactant-containing solution is treated, such as by heating or pressure reduction, to remove the bulk of the $CO_2$ before regeneration of the reactant (either prior or subsequent to sulfur removal). Alternately, or if small quantities of $CO_2$ are absorbed, the $CO_2$ may simply be stripped in the regeneration zone.

As indicated, supra, the invention also provides in this embodiment for the regeneration of the reactant and the absorbent. Specifically, the loaded absorbent mixture and the reduced polyvalent metal chelate are regenerated by contacting the mixture in a regeneration zone or zones with an oxygen-containing gas. The oxygen-containing gas may be air, oxygen, or air-enriched with oxygen. The oxygen-containing gas accomplishes two functions, the stripping of the $CO_2$ from the loaded absorbent mixture, and the oxidation of the reduced reactant to a higher oxidation state. The oxygen (in whatever form supplied) is supplied in a stoichiometric equivalent or excess with respect to the amount of reactant present in the mixture. Preferably, the oxygen-containing gas is supplied in an amount of from about 1.2 to 3 times excess.

The particular type of gaseous stream treated is not critical, as will be evident to those skilled in the art. Streams particularly suited to removal of $H_2S$ and $CO_2$ by the practice of the invention are, as indicated, naturally occurring gases, synthesis gases, process gases, and fuel gases produced by gasification procedures, e.g., gases produced by the gasification of coal, petroleum, shale, tar sands, etc. Particularly preferred are coal gasification streams, natural gas streams and refinery feedstocks composed of gaseous hydrocarbon streams, especially those streams of this type having a low ratio of $H_2S$ and $CO_2$, and other gaseous hydrocarbon streams. The term "hydrocarbon streams", as employed herein, is intended to include streams containing significant quantities of hydrocarbon (both paraffinic and aromatic), it being recognized that such streams contain significant "impurities" not technically defined as a hydrocarbon. Again, streams containing principally a single hydrocarbon e.g., ethane, are eminently suited to the practice of the invention. Streams derived from the gasification and/or partial oxidation of gaseous or liquid hydrocarbon may be treated by the invention. The $H_2S$ content of the type of streams contemplated will vary extensively, but, in general, will range from about 0.1 percent to about 10 percent by volume. $CO_2$ content may also vary, and may range from about 0.5 percent to over 99 percent by volume. Obviously, the amounts of $H_2S$ and $CO_2$ present are not generally a limiting factor in the practice of the invention.

The temperatures employed in the contacting or absorption-contact zone are not generally critical, except that the reaction is carried out at a temperature below the melting point of sulfur, and, if an absorbent is used, they must permit acceptable absorption of $CO_2$. In many commercial applications, such as the removal of $H_2S$ and $CO_2$ from natural gas to meet pipeline specifications, contacting at ambient temperatures is desired, since the cost of refrigeration would exceed the benefits obtained due to increased absorption at the lower temperature. In general, temperatures of from 10° C. to 80° C. are suitable, and temperatures from 20° C. to 45° C. are preferred. Contact times may range from about 1 second to about 270 seconds or longer, with contact times of 2 seconds to 120 seconds being preferred.

Similarly, in the regeneration or stripping zone or zones, temperatures may be varied widely. Preferably, the regeneration zone should be maintained at substantially the same temperature as the absorption zone. If heat is added to assist regeneration, cooling of the absorbent mixture is required before return of the absorbent mixture to the absorption zone. In general, temperatures of from about 10° C. to 80° C., preferably 20° C. to 45° C. may be employed.

Pressure conditions in the absorption zone may vary widely, depending on the pressure of the gas to be treated. For example, pressures in the absorption zone may vary from one atmosphere up to one hundred fifty or even two hundred atmospheres. Pressures of from one atmosphere to about one hundred atmospheres are preferred. In the regeneration on desorption zone or zones, pressures may be varied considerably, and will preferably range from about 0.5 atmosphere to about three or four atmospheres. The pressure-temperature relationships involved are well understood by those skilled in the art, and need not be detailed herein. Other conditions of operation for this type of reaction process, e.g. pH, etc., are further described in U.S. Pat. No. 3,068,065 to Hartley, et al, dated Dec. 11, 1962, and U.S. Pat. No. 4,009,251 to Meuly, issued Feb. 22, 1977, which disclosures are incorporated herein by reference. Preferably, pH in the process of the invention will range from about 6 to about 7.5, and the molar ratio of the nitrilotriacetic acid to the iron is from about 1.2 to 1.4. The procedure is preferably conducted continuously.

As indicated, the $H_2S$, when contacted, is quickly converted by a solution of Fe(III) chelate of nitrilotriacetic acid to elemental sulfur. The chelate is preferably supplied in admixture with water and a liquid absorbent. The amount of chelate compound, supplied is an effective amount, i.e., an amount sufficient to convert all or substantially all of the $H_2S$ in the gas stream, and will generally be on the order of at least about two mols per mol of $H_2S$. Ratios of from or about 2 mols to about 15 mols of chelate per mol of $H_2S$ may be used, with ratios of from about 2 mols per mol to about 5 mols of chelate per mol of $H_2S$ being preferred. The manner of preparing the admixture containing an absorbent is a matter of choice. For example, the chelate may be added to the absorbent, and, if necessary, then water added. The amount of water added will normally be just that amount necessary to achieve solution of the chelate, and can be determined by routine experimentation. Since the chelate may have a significant solubility in the solvent, and since water is produced by the reaction of the $H_2S$ and the chelate, precise amounts of water to be added cannot be given. In the case of absorbents having a low solubility for the chelate, approximately 5 percent to 10. percent water by volume, based on the total volume of the absorbent mixture, will generally provide solvency. Preferably, however, the chelate is added as an aqueous solution to the liquid absorbent. Where the chelate is supplied as an aqueous solution, the amount of solution supplied may be about 20 percent to about 80 percent by volume of the total absorbent admixture supplied to the absorption zone. The chelate solution will generally be supplied as an aqueous solution having a concentration of from about 0.1 molar to about 1.5 molar, and a concentration of about 1.0 molar is preferred.

The absorbents employed in this invention are those absorbents which have a high degree of selectivity in absorbing $CO_2$ (and preferably $H_2S$ as well) from the gaseous streams. Any of the known absorbents conventionally used which do not affect the activity of the chelating agent and which exhibit sufficient solubility for the reactant or reactants may be employed. As indicated, the absorbent preferably has good absorbency for $H_2S$ as well, in order to assist in the removal of any $H_2S$ present in the gaseous streams. The particular absorbent chosen is a matter of choice, given these qualifications, and selection can be made by routine experimentation. For example, diethylene glycol monoethyl ether, propylene carbonate, tetraethylene glycol-dimethyl ether, N-methyl pyrrolidone, sulfolane, methyl isobutyl ketone, 2,4-pentanedione, 2,5-hexanedione, diacetone alcohol, hexyl acetate, cyclohexanone, mesityl oxide, and 4-methyl-4-methoxy-pentone-2 may be used. Suitable temperature and pressure relationships for different $CO_2$-selective absorbents are known, or can be calculated by those skilled in the art.

As indicated, compounds having the formula $C_nH_{2n-1}OH$, in which n is a whole number from 4 through 22, preferably from 4 through 18, and mixtures thereof, may be used in improving the size of the sulfur particles produced. Most preferably, the compounds employed are those wherein n is a whole number from 8 through 18. Particularly preferred compounds are oleyl alcohol; 3-buten-1-ol; 1-hepten-4-ol-4-methyl, and mixtures thereof. The compound or compounds are supplied in an effective or modifying amount, i.e., an amount sufficient to improve the quality of the sulfur produced. This amount may be determined by experimentation, it being generally observed that the higher the molecular weight of the alcohol employed, the lower the concentration required to improve sulfur quality. Again, those skilled in the art may adjust the amount of modifier added to produce optimum results, good results being obtained, in the case of aqueous mixtures, when the modifier is present in an amount which is at or near the saturation level of the modifier in the reaction solution without forming a significant second layer. The manner of recovering the crystals is a matter of choice. For example, the crystals may be recovered by settling, filtration, liquid flotation, or by suitable devices such as a hydroclone, etc.

DETAILED DESCRIPTION OF THE INVENTION

In order to describe the invention in greater detail, the following experiments were run. The values given herein relating to temperatures, pressures, compositions, etc., should be considered merely exemplary and not as delimiting the invention.

EXAMPLE I $H_2S$ enters a contact vessel into which also enters an aqueous mixture containing 1.5 percent by weight Fe (based on the total weight of the mixture) as the Fe(III) chelate of nitrilotriacetic acid (NTA). The ligand was supplied in 40 percent molar excess, basis the iron, and the pH of the system was 7. The pressure of the feed gas is about 0 psig, and the temperature of the mixture is about 35° C. A contact time of about 120 seconds is employed. In the mixture, the $H_2S$ is converted to elemental sulfur by the Fe(III) chelate, Fe(III) chelate in the process being converted to the Fe(II) chelate. The sulfur produced is very fine and difficult to separate from solution, and has a mean volume diameter ($\mu$) by Coulter Counter of 5.8.

EXAMPLE II

A procedure similar to Example I was followed, except that 300 PPM by weight (based on the total weight of the mixture) of oleyl alcohol is added to the reactant solution. The sulfur crystals are larger than those of Example I, the mean volume diameter ($\mu$) being 7.1.

EXAMPLE III

A procedure similar to Example I was followed, using two different concentrations of 3-buten-1-ol. The results are shown in the Table.

TABLE

Effect of Modifiers on Sulfur Crystal Size of Reaction Solution at 60° C.

| Solution Composition | | | | |
|---|---|---|---|---|
| % w Fe | % m excess NTA | pH | Modifier | S° mean vol diameter ($\mu$)[b] |
| 1.5 | 40 | 7 | 3-buten-1-ol (1.5% wt.)[a] | 6.4 |
| 1.5 | 40 | 7 | 3-buten-1-ol (7.5% wt.)[a] | 10.3 |

[a] % wt. calculated basis solution without modifier.
[b] determined by Coulter Counter.

While the invention has been illustrated with particular apparatus, those skilled in the art will appreciate that, except where specified, other equivalent or analogous units may be employed. The term "zones", as employed in the specification and claims, includes, where suitable, the use of segmented equipment operated in series, or the division of one unit into multiple units because of size constraints, etc. For example, an absorption column might comprise two separate columns in which the solution from the lower portion of the first column would be introduced into the upper portion of the second column, the gaseous material from the upper portion of the first column being fed into the lower portion of the second column. Parallel operation of units is, of course, well within the scope of the invention.

Again, as will be understood by those skilled in the art, the solutions or mixtures employed may contain other materials or additives for given purposes. For example, U.S. Pat. No. 3,933,993 discloses the use of buffering agents, such as phosphate and carbonate buffers. Similarly, U.S. Pat. No. 4,009,251 describes various additives, such as sodium oxalate, sodium formate, sodium thiosulfate, and sodium acetate, which may be beneficial.

What is claimed is:

1. A process for the removal of $H_2S$ from a sour gaseous stream comprising:
   (a) contacting the sour gaseous stream in a contacting zone with an aqueous reaction solution at a temperature below the melting point of sulfur, the mixture comprising an effective amount of the ferric chelate of nitrilotriacetic acid and a modifying amount of a modifier selected from compounds having the formula $C_nH_{2n-1}OH$, wherein n is a whole number from 4 to 22, and mixtures thereof, to produce a sweet gas stream and an aqueous admixture containing crystalline sulfur and a reduced reactant;
   (b) removing at least a portion of the crystalline sulfur from the aqueous admixture;
   (c) regenerating the aqueous admixture in a regenerating zone with oxygen to produce a regenerated reactant; and
   (d) returning aqueous admixture from the regeneration zone to the contacting zone.

2. The method of claim 1 wherein the stream from which the $H_2S$ is removed is selected from naturally occurring gases, synthesis gases, process gases, and fuel gases, and wherein the sulfur is removed by filtration.

3. The method of claim 1 wherein the sour gaseous stream is selected from natural gas, a stream derived from the gasification of coal, or a hydrocarbon stream, and n is a whole number from 4 through 18.

4. A process for the removal of $H_2S$ from a sour gaseous stream comprising:
   (a) contacting the sour gaseous stream in a contacting zone with an aqueous reaction solution at a temperature below the melting point of sulfur, the mixture comprising an effective amount of the ferric chelate of nitrilotriacetic acid and a modifying amount of a modifier selected from compounds having the formula $C_nH_{2n-1}OH$, wherein n is a whole number from 4 through 18, and mixtures thereof, to produce a sweet gas stream and an aqueous admixture containing crystalline sulfur and a reduced reactant;
   (b) regenerating the aqueous admixture in a regeneration zone with oxygen to produce a regenerated reactant;
   (c) removing at least a portion of the crystalline sulfur from the aqueous admixture; and
   (d) returning aqueous admixture from step (c) to the contacting zone.

5. The method of claim 4 wherein the stream from which the $H_2S$ is removed is selected from naturally occurring gases, synthesis gases, process gases, and fuel gases, and wherein the sulfur is removed by filtration.

6. The method of claim 4 wherein the sour gaseous stream is selected from natural gas, a stream derived from the gasification of coal, or a hydrocarbon stream, and n is a whole number from 4 through 18.

7. A process for the removal of $H_2S$ and $CO_2$ from a sour gaseous stream comprising:
   (a) contacting the sour gaseous stream in a contacting zone at a temperature below the melting point of sulfur with a lean $CO_2$-selective absorbent mixture containing an effective amount of the Fe(III) chelate of nitrilotriacetic acid and a modifying amount of a modifier selected from compounds having the formula $C_nH_{2n-1}OH$, wherein n is a whole number from 4 through 22, and mixtures thereof, and producing a sweet gaseous stream and an absorbent admixture containing absorbed $CO_2$, sulfur, and Fe(II) chelate of nitrilotriacetic acid,
   (b) removing sulfur from the absorbent admixture, and leaving a solution containing absorbed $CO_2$ and Fe(II) chelate of nitrilotriacetic acid,
   (c) stripping the solution containing absorbed $CO_2$ and said Fe(II) chelate, and regenerating Fe(III) chelate of nitrilotriacetic acid in said solution with oxygen, producing a lean $CO_2$-selective absorbent solution containing the Fe(III) chelate of nitrilotriacetic acid, and (d) returning lean CO$_2$-selective absorbent solution containing Fe(III) chelate of nitrilotriacetic acid to the contacting zone.

8. A process for the removal of H$_2$S and CO$_2$ from a sour gaseous stream comprising:
   (a) contacting the sour gaseous stream in a contacting zone at a temperature below the melting point of sulfur with a lean CO$_2$-selective absorbent solution containing an effective amount of the Fe(III) chelate of nitrilotriacetic acid and a modifying amount of a modifier selected from compounds having the formula C$_n$H$_{2n-1}$OH, wherein n is a whole number from 4 through 22, and mixtures thereof, and producing a sweet gaseous stream and an absorbent mixture containing absorbed CO$_2$, sulfur, and Fe(II) chelate of nitrilotriacetic acid,
   (b) stripping the solution containing absorbed CO$_2$, sulfur, and said Fe(II) chelate, and then regenerating the Fe(III) chelate of nitrilotriacetic acid in said solution with oxygen, producing a lean CO$_2$-selective absorbent solution containing the Fe(III) chelate of nitrilotriacetic acid, and sulfur,
   (c) removing sulfur from the lean CO$_2$-selective absorbent solution containing the sulfur and the Fe(III) chelate of nitrilotriacetic acid, and leaving a lean CO$_2$-selective absorbent solution containing the Fe(III) chelate of nitrilotriacetic acid, and
   (d) returning lean CO$_2$-selective absorbent solution containing the Fe(III) chelate of nitrilotriacetic acid to the contacting zone.

9. A process for the removal of H$_2$S and CO$_2$ from a sour gaseous stream comprising:
   (a) contacting the sour gaseous stream in a contacting zone at a temperature below the melting point of sulfur with a lean CO$_2$-selective absorbent mixture containing an effective amount of the Fe(III) chelate of nitrilotriacetic acid and a modifying amount of a modifier selected from compounds having the formula C$_n$H$_{2n-1}$OH, wherein n is a whole number from 4 through 22, and mixtures thereof, and producing a sweet gaseous stream and an absorbent admixture containing absorbed CO$_2$, sulfur, and Fe(II) chelate of nitrilotriacetic acid,
   (b) removing sulfur from the absorbent admixture, and leaving a solution containing absorbed CO$_2$ and Fe(III) chelate of nitrilotriacetic acid,
   (c) stripping the solution containing absorbed CO$_2$ and said Fe(II) chelate and regenerating the Fe(III) chelate of nitrilotriacetic acid in said solution with oxygen, producing a lean CO$_2$-selective absorbent solution containing the Fe(III) chelate of nitrilotriacetic acid, and
   (d) returning the lean CO$_2$-selective absorbent solution containing the Fe(III) chelate of nitrilotriacetic acid to the contacting zone.

10. A process for the removal of H$_2$S and CO$_2$ from a sour gaseous stream comprising:
    (a) contacting the sour gaseous stream in a contacting zone at a temperature below the melting point of sulfur with a lean CO$_2$-selective absorbent solution containing an effective amount of the Fe(III) chelate of nitrilotriacetic acid and a modifying amount of a modifier selected from compounds having the formula C$_n$H$_{2n-1}$OH, wherein n is a whole number from 4 through 22, and mixtures thereof, and producing a sweet gaseous stream and an absorbent mixture containing absorbed CO$_2$, sulfur, and the Fe(II) chelate of nitrilotriacetic acid,
    (b) stripping the solution containing absorbed CO$_2$, sulfur and the said Fe(II) chelate and regenerating the Fe(III) chelate of nitrilotriacetic acid in said solution with oxygen, producing a lean CO$_2$-selective absorbent solution containing the Fe(III) chelate of nitrilotriacetic acid and sulfur,
    (c) removing sulfur from the lean CO$_2$-selective absorbent solution containing the sulfur and the Fe(III) chelate of nitrilotriacetic acid, and leaving a lean CO$_2$-selective absorbent solution containing the Fe(III) chelate of nitrilotriacetic acid, and
    (d) returning lean CO$_2$-selective absorbent solution containing the Fe(III) chelate of nitrilotriacetic acid to the contacting zone.

11. The process of claim 7 wherein the lean CO$_2$-selective absorbent mixture comprises an absorbent selected from diethylene glycol monoethyl ether, propylene carbonate, tetraethylene glycol-dimethylether, N-methyl pyrrolidone, sulfolane, methyl isobutyl ketone, 2,4-pentanedionne, 2,5-hexanedione, diacetone alcohol, hexyl acetate, cyclohexane, mesityl oxide, and 4-methyl-4-methoxy-pentene-2.

12. The process of claim 8 wherein the lean CO$_2$-selective absorbent mixture comprises an absorbent selected from diethylene glycol monoethyl ether, propylene carbonate, tetraethylene glycol-dimethylether, N-methyl pyrrolidone, sulfolane, methyl isobutyl ketone, 2,4-pentanedionne, 2,5-hexanedione, diacetone alcohol, hexyl acetate, cyclohexane, mesityl oxide, and 4-methyl-4-methoxy-pentene-2.

13. The process of claim 9 wherein the lean CO$_2$-selective absorbent mixture comprises an absorbent selected from diethylene glycol monoethyl ether, propylene carbonate, tetraethylene glycol-dimethylether, N-methyl pyrrolidone, sulfolane, methyl isobutyl ketone, 2,4-pentanedionne, 2,5-hexanedione, diacetone alcohol, hexyl acetate, cyclohexane, mesityl oxide, and 4-methyl-4-methoxy-pentene-2.

14. The process of claim 10 wherein the lean CO$_2$-selective absorbent mixture comprises an absorbent selected from diethylene glycol monoethyl ether, propylene carbonate, tetraethylene glycol-dimethylether, N-methyl pyrrolidone, sulfolane, methyl isobutyl ketone, 2,4-pentanedionne, 2,5-hexanedione, diacetone alcohol, hexyl acetate, cyclohexane, mesityl oxide, and 4-methyl-4-methoxy-pentene-2.

* * * * *